United States Patent [19]

Guéritée

[11] 4,278,668

[45] Jul. 14, 1981

[54] PURE 17 ALPHA-ETHYNYL(5 ALPHA), ANDROST-2-ENE,17 BETA-CL, PROCESS FOR ITS PREPARATION AND THERAPEUTICAL APPLICATIONS OF THE SAME

[76] Inventor: Nicolas Guéritée, 65 rue des Vignes, Paris, France, 75016

[21] Appl. No.: 58,010

[22] Filed: Jul. 16, 1979

Related U.S. Application Data

[63] Continuation-in-part of Ser. No. 854,757, Nov. 25, 1977, abandoned.

[51] Int. Cl.$^3$ .................... A61K 31/56; A01N 45/00
[52] U.S. Cl. .................... 424/238; 260/397.5; 260/397.3
[58] Field of Search ...................... 260/397.5

[56] References Cited

U.S. PATENT DOCUMENTS 2,996,524  8/1961  Huffman ...................... 260/397.5

*Primary Examiner*—Elbert L. Roberts
*Attorney, Agent, or Firm*—Gifford, VanOphem, Sheridan & Sprinkle

[57] ABSTRACT

The delta-2 isomer of the 17 alpha-ethynyl (5 alpha), 2-androsten, 17 beta-ol, unmixed with its delta-3 isomer; a process for making the therapeutic isomer and its 17 beta-acetate; and a method of treatment of endometriosis with the 17 beta-acetate of the delta-2 isomer. The pure delta-2 isomer of 17 alpha-ethynyl (5 alpha), 2-androsten, 17 beta-ol, unmixed with its delta-3 isomer, is obtained by oxidation of the isomeric precursor 17-keto (5 alpha), 2-androsten with Jones Reagent. The 17 beta-acetate of the delta-2 isomer of the beta-ol is effective in the treatment of endometriosis by the administration of a daily dose of about 100 to 300 milligrams.

7 Claims, No Drawings

PURE 17 ALPHA-ETHYNYL(5 ALPHA), ANDROST-2-ENE,17 BETA-OL, PROCESS FOR ITS PREPARATION AND THERAPEUTICAL APPLICATIONS OF THE SAME

CROSS REFERENCE

This is a continuation-in-part of U.S. application Ser. No. 854,757, filed on Nov. 25, 1977, now abandoned.

BACKGROUND OF THE INVENTION

1. Field of the Invention

This invention, in the capacity of a new drug, possessing several applications in clinics, is concerned with the chemical substance of the following formula:

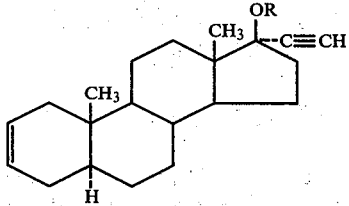

in which R represents hydrogen or an acetyl residue.

The chemical denomination of the compound is therefore: 17 alpha-ethynyl(5 alpha), 2-androsten,17 beta-ol (and its 17 beta-acetate).

2. Description of the Prior Art

Several authors and, namely, M. HUFFMAN (U.S. Pat. No. 2,996,524) J. A. EDWARDS and A. BOWERS (Chemistry and Industry, 1961, p. 1962-1963) and D. POMONIS & al. (Cancer Chemotherapy Reports, 1962, Sept. 31-32), described a process for obtaining a substance to which they thought they could attribute the structure and chemical formula of 17 alpha-ethynyl(5 alpha), 2-androsten,17 beta-ol (and its acetate), possessing properties that:

stimulate the reticulo-endothelial system, inhibit the gonads by suppressing the pituitary gonadotrophins.

When establishing the analytical file of a drug containing the substance prepared according to the teaching of M. Huffman in Example 8 of U.S. Pat. No. 2,996,524, as demanded by the Health Authorities of all countries, in order to be assured of the purity of the said substance, the applicant discovered that this process led, not to the pure product (I), but to a mixture of this product (I) with its delta-3 isomer (II), the latter in varying proportions from one batch to another, but always in unacceptable proportions, e.g. roughly 20%.

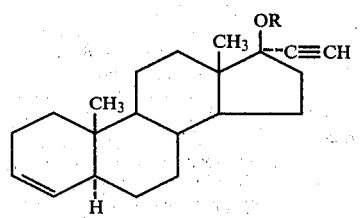

On further analytical study, the applicant also discovered that the raw material used by the method described by Huffman in U.S. Pat. No. 2,996,524 and improperly designated as 17-keto(5 alpha), 2-androsten, was itself a mixture of isomers delta-2 and delta-3 and this was the reason it was not possible for the final product to be pure.

The identical polarity of these two isomers makes their separation by the classical methods of chromatography impossible; now, it is well-known that the usual methods of preparation of steroids of this chemical family inevitably lead to mixtures of isomers delta-2 and delta-3 which are not possible to separate (J. FAJKOS & al., Czech.Chem.Comm., 1959,24: 3115–3135; P. D. KLIMSTRA, J.Med.Chem, 1965, 8: 45–52).

Health Authorities do not accept products for therapeutical use unless their purity is invariable and compatible with the safety of the patients. The applicant was therefore obliged to continue his investigations until he discovered the method of preparative purification as embodied by this invention and which enabled him to eliminate the delta-3 isomer from the raw material.

SUMMARY OF THE INVENTION

This invention relates to the discovery of the sensitivity of isomer delta-3 to Jones reagent, thereby contrasting with the lack of sensitivity of isomer delta-2 to this reagent (which is a solution of chromic anhydride in acetone, in the presence of $H_2SO_4$: BODEN, K.; HEILBRON, L. N.; JONES, E. R. H.; WEEDON, E., Journal Chem.Soc., 1946: 39).

Therefore, the method of preparation of pure compound delta-2, as embodied by this invention, consists in the treatment of the raw material i.e. the mixture of 17-keto(5-alpha),2-androsten with 17-keto(5 alpha),3-androsten, with Jones reagent: isomer delta-3 is oxidised, probably into a corresponding diacid or aldehyde and thus its polarity becomes different from that of isomer delta-2; this enables the latter to be collected, practically pure, by silica gel chromatography.

From this point, pure 17-keto, (5 alpha), 2-androsten, after undergoing the reaction described in example No. 8 of the U.S. Pat. No. 2,996,524 leads to 17 alpha-ethynyl, (5 alpha), 2-androsten,17 beta-ol but in pure form, which is the product concerned by the present invention.

DESCRIPTION OF THE PREFERRED EMBODIMENT

The following is a method of preparation consisting in a first stage, according to the present invention, in the separation of the 17-keto, (5 alpha) androsten-2 and -3 isomers and then, in a second stage, in the preparation of the product, in free alcohol form, and then, in a third stage in the preparation of its 17-beta acetate.

EXAMPLE

Stage 1: Separation of a mixture of 17-keto (5 alpha),androsten-2 and 3-isomers 20 g of the steroid in 400 cc of acetone solution are introduced in a 1 liter flask with magnetic stirring. It is cooled to −20° C. and 60 cc Jones reagent are added, drop by drop. The flask is shaken for 1¼ hours to return to room temperature. 100 cc methanol are then added and the mixture shaken for 15 minutes. The solvents are distilled and the residue taken up in 700 cc water. The precipitate is filtered and washed with water, then dissolved in 500 cc methylene chloride. The organic solution is dried with sodium sulphate and distilled. The residue (18,5 g) is purified by silica column chromatography. Elution with benzene produces 11 g of pure "DELTA-2" derivative. The study of the NMR spectrum (CDCl3, TMS) of this derivative shows olefinic protons at C2 and C3 as a broad singlet at 334 Hz (ΔW/2:5 Hz), while in derivative "DELTA-3", the olefinic protons appear as 4 broad signals between 312 and 348 Hz.

Stage 2: Preparation of 17 alpha-ethynyl,(5 alpha), 2-androsten,17 beta-ol not mixed with isomer delta-3

1,2 g of potassium is dissolved in 30,5 ml of anhydrous t-amyl alcohol. A solution of 1.1 g of pure 2-androsten-17-one, obtained as indicated in Stage 1 above, in 40 ml of anhydrous toluene is added and nitrogen is passed through the mixture to dispel air. The resulting solution is stirred for 15 hours while a slow stream of purified anhydous acetylene is bubbled through. At the end of this period, 300 ml of ice water are added. The pH is adjusted to 1 with 50% aqueous hydrochloric acid. The resulting solution is distilled to remove all volatile organic materials. It is cooled to 0° C., extracted with ether, and the ether extract is washed with water, dried with sodium sulphate and evaporated. The residue of 17 alpha-ethynyl,(5 alpha) 2-androsten-17 beta-ol is recrystallised from hexane.

Stage 3: Preparation of 17 beta acetate of 17 alpha-ethynyl, (5-alpha), 2-androsten, 17 beta-ol 600 mg of paratoluenesulphonic acid are introduced into a solution of 600 mg of 17 alpha-ethynyl, 2-androsten,17 beta-ol in 10 cm³ acetic anhydride. The solution thus obtained was allowed to rest at 20° C. for 18 hours, protected from air. It was then poured into 200 cm³ ice water and the mixture cooled for 3 hours. The precipitate of 17 alpha-ethynyl,(5 alpha),2-androsten, 17 beta-acetate is collected by filtering; it is washed with water, then dried and recrystallised from methanol.

I. Physical properties of Compounds I & II and their mixture

After having thus prepared pure compound "DELTA-2" (I), the applicants also synthesised pure isomer "DELTA-3" (II) so as to obtain the counter-proof of his discovery by the reconstitution of the physico-chemical characteristics of the substance described by Huffman in Example 8 of U.S. Pat. No. 2,966,524 with the mixture, this time intentional, of the two pure compounds in the proportions of 80 to 20.

The synthesis of pure compound "DELTA-3" was performed according to the following reaction, starting from testosterone:

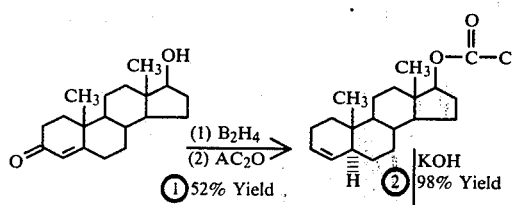

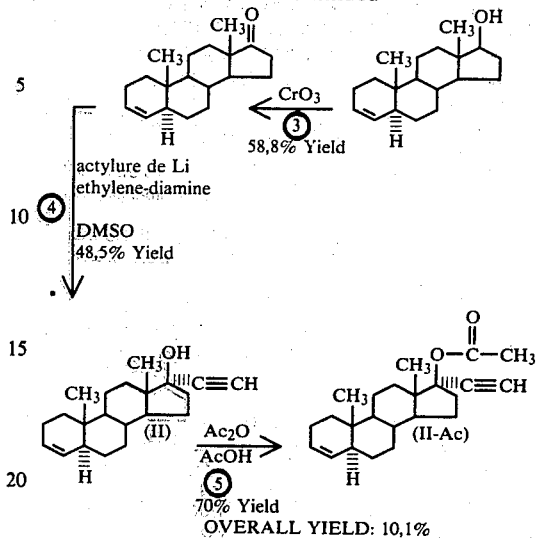

OVERALL YIELD: 10,1%

The following tables and figures show the physical characteristics of the various compounds obtained or reconstituted. To simplify the following, the product obtained from the process described in Example 8 of U.S. Pat. No. 2,996,524 will hereinafter be referred to by the abbreviation "MIX" and each of the pure compound I and II, in acetate form (R=acetoxy) will hereinafter be referred to respectively as "Δ-2" and "Δ-3", (or respectively "DELTA-2" and "DELTA-3").

TABLE I

| Compounds | Melting points (Koffler) Degrees C. |
|---|---|
| pure Δ-2 | 160–162 |
| pure Δ-3 | 198–199 |
| product of Example 8 (MIX) U.S. Pat. No. 2,996,524 | 140.5–141 |
| mixture reconstituted by the applicant: Δ-2 + Δ-3 | 140–168 (according to the proportions) |

TABLE II

| | NMR spectra, between 300 and 350 Hz (band corresponding to the ethylene protons) |
|---|---|
| Pure Δ-2, according to the invention | Signal assimilated to a singlet, centered on approximately 335 Hz |
| Pure Δ-3 prepared by the Applicant | Multiplet, in a first approximation, constituted by two doubled doublets "HA" and "HB", corresponding to ethylene protons at C3 and C4, respectively situated at 330 Hz and 315 Hz approximately, and the coupling constant at 10 Hz. The fine structure of this multiplet is due to the allyl and homo allyl coupling of the protons next to the ethylene protons |
| Reconstituted mixture: 80% pure Δ-2 and 20% pure Δ-3 | Superimpositing of the two basic spectra: the signal of the proton at Δ-2 partly covers the "HA" signal of the multiplet due to the proton at Δ-3; the "HB" part of this multiplet appears clearly, centered at approximately 315 Hz. |
| Mixture obtained from the method specified in Example 8 of U.S. Pat. No. 2,996,524 (MIX) | Spectrum analogous to that of the reconstituted mixture The differences are due to the background noise linked with the |

TABLE II-continued

NMR spectra, between 300 and 350 Hz (band corresponding to the ethylene protons)

| Pure Δ-2, according to the invention | Signal assimilated to a singlet, centered on approximately 335 Hz |
|---|---|
|  | amplitude of registration of the spectrum. |

Some of the differences in the chemical displacement are due to the variations in the original calibration (offset).

These tests, therefore, clearly prove that the substance obtained by Huffman was not at all pure, the proportion of isomer Δ-3 contaminating compound Δ-2 being approximately 20%.

It is to be noted that the discoveries, as embodied by this invention, could not have been possible without the development of the technique of nuclear magnetic resonance. Access to this technique was exceptional in March 1961, date on which Huffman submitted his application for U.S. Pat. No. 2,996,524, since the first utilisation in organic chemistry was described in literature only in 1959 (J. D. ROBERTS, Nuclear Magnetic Resonance. Applications to Organic Chemistry—Mc-Graw-Hill, N.Y. 1959; J. A. POPLE & al., High-resolution Nuclear Magnetic Resonance, Mc Graw-Hill, 1959; L. M. JACKMAN, Applications of Nuclear Magnetic Resonance Spectroscopy in Organic Chemistry. Pergamon Press, N.Y. 1959). This is most probably the reason Huffman was unaware that his process resulted in a mixture of isomers, of identical polarity, and not in the pure substance, the structure of which he believed he had described.

II. Biological properties of pure compound Δ-2

The applicant performed a large number of studies to check whether the biological activities of pure compound Δ-2 were identical or not to those described in U.S. Pat. No. 2,996,524.

He noted that compound Δ-2 possesses not only properties other than those claimed by the U.S. patent (e.g. protection of the bone against the destructive effect of the parathormone) but, further, in certain respects, its properties are even the opposite of what had previously been disclosed (e.g. a stimulating and not inhibiting, clomiphene-like effect of the pituitary gonadotrophic hormones under certain experimental conditions).

A. Compound "DELTA-2", contrary to what was stated in previous literature which, in fact, concerned "MIX", is a stimulator of the gonads, therefore possessing under certain conditions, but by different routes, a clomiphene-like stimulating effect on the pituitary gonadotrophins. This discovery is useful for the treatment of ovarian or testicular dysfunction, including some forms of sterility.

Clomiphene, a classical gonadotrophic stimulant, used for the treatment of pituitary gonadic dysfunction, amongst which female sterility due to anovulation, was obviously used as standard in several series of experiments which revealed the clomiphene-like effects of 17 alpha-ethynyl, (5 alpha), 2-androsten, 17 beta acetate.

(a) In adult female rats, an appropriate dose of clomiphene, injected at a particular moment of the cycle, prevents ovulation in 100% of the animals (DOCKE, J. Reprod. Fertility 1971, 24: 45–54).

The following table shows that compound "DELTA-2" has qualitative effects, analogous to those of clomiphene, in this method.

TABLE III

|  | % of ovulating animals | Number of ova | | |
|---|---|---|---|---|
|  |  | left ovary | right ovary | mean total |
| Controls | 100% | 5 to 9 | 5 to 9 | 13.5 |
| Clomiphene s.c. single dose 3 mg/kg | 0 | 0 | 0 | 0 |
| "DELTA-2" s.c. 1.8 mg/kg/day × 3 | 40% | 7 to 8 | 6 to 8 | 14.5 |
| "DELTA-2" s.c. 5.4 mg/kg/day × 3 | 60% | 6 to 10 | 5 to 8 | 14 |

This first experiment was only a screening; further it permitted to note that the weakest dose administered (1.8 mg/kg/day × 3) already produces the maximum effect.

When the experiment was repeated, with the administration of single doses of "DELTA-2" of 1.8 mg and 5.4 mg/kg at various moments of the cycle, it showed that the effectiveness of "DELTA-2" is even more similar so that of clomiphene from both qualitative and quantitative points of view, if the steroid is administered at the metestrus and at the proestrus:

TABLE IV

|  |  | % of ovulation if injected: | |
|---|---|---|---|
|  |  | at metestrus | at proestrus |
| "DELTA-2" | 1.8 mg/kg | 25 | 80 |
|  | 5.4 mg/kg | 40 | 20 |

(b) In immature female rats, ovulation can be provoked in 80% of the animals by the injection of a relatively low dose (4 I.U.) of gonadotrophins (Pregnant Mare Serum, or PMS). By this method, both clomiphene and "DELTA-2" at a low dose, cause a decrease in the percentage of ovulating rats:

TABLE V

| Controls | : 4 I.U. PMS | 80% ovulation |
|---|---|---|
|  | : 4 I.U. PMS + clomiphene (3 mg/kg) | 30% ovulation |
|  | : 4 I.U. PMS + "DELTA-2" (0.6 mg/kg) | 20% ovulation |
|  | : 4 I.U. PMS + "DELTA-2" (1.8 mg/kg) | 100% ovulation |

The mechanisms of the phenomenon is as follows: PMS causes the ovary to secrete an adequate quantity of estrogens which induces the release of the LH pituitary gonadotrophin which, in turn, triggers off ovulation.

Clomiphene, which is an anti-estrogen, prevents the estrogens, secreted under the effect of PMS, from acting on the pituitary: there is no LH release and therefore no ovulation.

"DELTA-2" is not an anti-estrogen. Theroetically, the anti-ovulatory effect it has at low doses (0.6 mg/kg) can only be explained by one of the following hypotheses:

(1) inhibition of the release of the LH gonadotrophin by the pituitary, (2) inhibition in the ovary of the secretory response to the PMS solicitation, (3) and/or, in the ovary, inhibition of the ovulatory response to the LH which was eventually released after estrogen stimulation.

At the strong dose (1.8 mg/kg), it was noted that compound "DELTA-2" maintains and even stimulates ovulation; in this manner it behaves like a direct pituitary stimulant by acting as a releasing factor of FSH and LH, or of the LH-RH hypothalamic hormone.

In clinics, compound "DELTA-2" acts like LH-RH by increasing the release of FSH and LH, even when it is already excessive (e.g. Klinefelter's syndrome) and even when the excess is consecutive to a genetic absence of gonads (e.g. Turner's syndrome).

When stronger doses of PMS (8 I.U.) are administered, an (inverse) confirmation of the clomiphene-like effect of "DELTA-2" is obtained and the second of the three theoretical mechanisms mentioned above becomes the most probable, namely, the inhibition in the ovary of the secretory response to PMS stimulation.

The following table shows the results of 4 series of experiments.

In practice, the application of these effects concern the treatment of some endocrine tumours that are not only pituitary-dependent (which would stem logically from previous publications) but also non-pituitary-dependent.

(a) The direct gonad-inhibiting effects of "DELTA-2" take place at the same time as pituitary gonadotrophic suppression.

In female rats, the autograft of a fragment of an ovary into the omentum, immediately following bilateral ovariectomy, causes the derivation to the liver of the gonadal hormones and their destruction in this organ. A strong, permanent, reactional increase in the production of pituitary gonadotrophins follows, which causes tumoral proliferation of the ovarian graft (the histological findings of the pituitary stimulated in this manner are characteristic).

A specifically pituitary-suppressing drug, like methallibure results, in this experiment, in a halt in the development of the graft and in the disappearance of the microscopic aspects of hyperstimulation of the pituitary

|  |  | Percentage of Ovulating Rats | | | | | | |
|---|---|---|---|---|---|---|---|---|
| Single s.c. injection | | 1st series | 2nd series | 3rd series | 4th series | cumulative results | number of animals | mean number of ova |
| Controls | 8 I.U. PMS | 0 | 0 | 25 | 14 | 9.5 | 21 | 1 |
| + CLOMIPHENE | 0.75 mg/kg | — | 50 | 25 | 14 | 27 | 15 | 7 |
|  | 1.5 mg/kg | — | 25 | — | — | 25 | 4 | 3 |
|  | 3 mg/kg | 20 | 0 | — | — | 11 | 9 | 3 |
|  | 6 mg/kg | — | 0 | — | — | 0 | 4 | 0 |
| + DELTA-2 | 0.6 mg/kg | 0 | — | 75 | 43 | 37 | 16 | 5 |
|  | 1.8 mg/kg | 20 | — | 50 | — | 30 | 10 | 8 |
|  | 5.4 mg/kg | 0 | — | 50 | — | 50 | 4 | 1.5 |

The two compounds are biologically analogous, but act differently:
- clomiphene is an anti-estrogen, thus preventing the inhibiting effect of the estrogens on the release of the LH gonadotrophin;
- steroid "DELTA-2" prevents the ovary from secreting the large quantity of estrogens demanded by the FSH stimulation.

B. Compound 17 alpha-ethynyl, (5 alpha), 2-androsten,17 beta-ol (in acetate form) is a direct gonad inhibitor under certain circumstances, and contrary to what could be expected from the physiological mechanism of feed-back, the gonad-inhibiting activity of "DELTA-2" is associated with inhibition of pituitary gonadotrophins.

(BER, A., Endokrinologie, 1968, 53: 62; ibid., 1968, 53, 237; Acta Endocrinologica 1972,70: 167).

The addition of an appropriate quantity of exogenous pituitary gonadontrophins (PMS) causes the resumption of the development of the tumour which had been stopped by methallibure. The administration of a substance "X" of which the effect is directly gonad-inhibiting, produces the involution of the graft and prevents the resumption of its development, under PMS stimulation. Compound "DELTA-2" acted in this manner (see Table VII below) when tested according to this method, with the following results:

TABLE VII

| Treatment | Dose/day (mg/kg or PMS I.U./animal) | Weight of graft (mg) | Weight of uterus (mg) |
|---|---|---|---|
| Grafted controls |  | 217.4 ± 16.4 | 58.6 ± 8 |
| + methallibure | 120 | 22.6 ± 2.4*** | 29 ± 4.5** |
| + methallibure | 120 |  |  |
| +PMS | 20 | 136.5 ± 24.5* | 77 ± 9.7 |
| methallibure + DELTA-2 | 3 | 136.7 ± 10.7** | 119.5 ± 14.9** |
| methallibure + DELTA-2 | 6 | 62.4 ± 9.9*** | 139.4 ± 10.4*** |
| + methallibure + PMS + DELTA-2 | 120 20  3 | 153.7 ± 35.2$^{(1)}$ | 128 ± 23.8* |
| + methallibure + PMS + DELTA-2 | 120 20  6 | 69.7 ± 9.8** | 124.8 ± 9.7*** |

$^{(1)}$Comparison with the batch: "methallibure + PMS"
*: $p < 0.05$;
**: $p < 0.01$;
***: $p < 0.001$ The following conclusions were drawn:

(1) "DELTA-2" alone causes involution of the ovariant graft which is statistically significant and proportionate to the doses administered;

(2) "DELTA-2", added to the methallibure+PMS system, also causes a statistically significant involution of the graft.

This is the proof that "DELTA-2" possesses a direct gonad-inhibiting effect which is claimed by the present invention as an unexpected discovery.

The histological study of the ovarian graft and of the pituitaries of the treated animals confirm this fact.

This direct anti-gonadal mechanism of compound "DELTA-2" coexists, in a surprising manner with a pituitary gonadotrophin-inhibiting effect.

This is another new and unexpected element of the present invention because it is the contrary to what would normally have been expected: according to the laws of physiology, any direct inhibition of the gonad automatically triggers off stimulation of the production and/or release of pituitary gonadotrophins by positive feed-back.

(b) Investigation on direct anti-tumoral activity by nonpituitary-dependent methods of experimental oncogenesis Compound "DELTA-2" is very active on some experimental gonadal tumours induced by methods of long-lasting gonadotrophic pituitary stimulation, analogous to the one described above.

After 45 days of oral treatment, the mean weight of the testicular tumour induced in rats after a one year latency period was $45+18.9$ mg, versus $2,533.3+260.3$ mg, mean weight of the tumour in the controls ($p<0.001$): complete remission was noted in half of the treated animals whilst all the controls maintained the tumours.

This difference between the tumours of the controls and those of the treated animals (weight and remission) is so considerable that it would be difficult to explain it by gonadotrophic pituitary suppression alone; it strongly suggests the addition of a directly anti-tumoural mechanism, such as described in the above experiments.

The direct anti-tumoural effect of "DELTA-2" was confirmed with non-pituitary-dependent, malignat tumours which were transplanted or inoculated.

One of these models is the mammary adenocarcinoma of the mouse (A. RIVENZON and A. MACRINEAU - Néoplasma 1968, 15:2) which, under the effect of "DELTA-2" disappeared in 33.3% of the mice (but present in all the controls) and with a mean weight reduced to $436.66 \pm 147.23$ mg (versus $1,713,33 \pm 189.19$ mg in the controls; $p<0.001$).

Another model is the ovarian ascitic tumour, of hyper-acute evolution which, in female rats, usually kills all the controls within 16 days after the intraperitoneal inoculation (E. POGOSIANZ and coll., Voprosi Onkologii, 1962, 8, 11:29–36).

On 16th day, under the effect of compound "DELTA-2", there are 93.3% survivors (against 20.6% in the controls) and after the sacrifice on 27th day, of the treated survivors, the rarity of tumoural cells in the peritoneum and omentum is noted as well as the absence of ganglion metastases and disappearance of the fluorescence which was intense in the controls, revealing the importance of the enzymatic activity linked with oncogenesis.

C. The anti-parathyroid properties of 17 alpha-ethynyl, (5-alpha), 2-androsten 17 beta-ol acetate are revealed not only on experimental parathyroid hyperplasia, but also in bone.

With regards to the latter, it is known that the parathyroid hormone (PTH) causes the destruction of bone with, as a consequence, the release of proportionate quantities of calcium. The effect and its eventual inhibition can be determined in bone tissue cultures (FELL, H. B., and WEISS, L., J.exp.Med.1965, 121:551–560).

Amongst the compounds likely to oppose the effect of PTH on bone are some estrogens (D. ATKINS et al., J.Endrocrinology 1972, 54:107–117); in this respect, the most active of them, ethynyl-estradiol, is used as standard when the antiosteolytic activity of another substance has to be determined The release of calcium by the mouse calvaria under the effect of 0.6 U. of PTH, in bone tissue culture, is inhibited:

from $137\% \pm 2\%$ by 200 µg ethynyl-estradiol, and
from $96\% \pm 6\%$ by 200 µg of DELTA-2

The apparent superiority of the standard disappears when the range of the usual human doses (depending on the indications) of the two steroids are compared:

10 to 100 µg per day, for ethynyl-estradiol, 5 to 300 mg per day, for "DELTA-2"

In clinics, daily doses of about 10 mg of "DELTA-2" caused the decrease in the excessive destruction of bone, which resulted in the decrease in both ratios between fasting urinary calcium and creatinin (B. E. C. NORDIN & al.) and in serum calcium, to below 100 mg/l.

III. Biological superiority of compound "DELTA-2" over its isomer "DELTA-3" and, consequently, on the association of both isomers ("MIX") as obtained by the previously described methods In young rats, unilateral ovariectomy causes compensatory hypertrophy of the remaining ovary, consequence of the positive feed-back triggered off by the operation. Treatment with a compound that is exclusively antigonadotrophic can, at most, eliminate the entire reactional hypertrophy: the weight of the remaining ovary is then the same as that of the ovaries of the non-spayed controls, i.e. inhibition which does not exceed 100%. A compound which causes a decrease in the weight of the remaining ovary, to below the weight of the non spayed control ovary (inhibition > 100%) obviously acts, at least in part, on the ovary itself. This is the mechanism of "DELTA-2", thereby confirming that it is active on both poles of the pituitary-gonadal axis.

The comparative study of isomers "DELTA-2" and "DELTA-3" was performed by this method because it supplies reproducible, homogeneous and quantifiable results.

A first experiment determined that "MIX", resulting from the preparation indicated in previous literature produced, at a dose of 120 µg/animal/day orally, a 121% inhibition of the remaining ovary which is highly significant ($p<0.001$), whilst pure isomer "DELTA-3", up to doses of 240 µg, only caused less than 50% inhibition which is not statistically significant.

A second experiment compared the effects of "MIX" with those of pure "DELTA-2" and "DELTA-3" separately. The following table VIII indicates these results.

TABLE VIII

| Treatment (μg/animal/day) | | MEAN WEIGHT | | | % of inhibition |
|---|---|---|---|---|---|
| | | of body (g) | of uterine horns (mg) | of ovary (mg) | |
| ½ spayed controls | | 108.6 | 103 | 20.7 | |
| Controls | | 106.8 | 81,3 | 12.4** | 100 |
| S.C. estradiol:0.2 | | 113.2 | 131.9 | 13.9* | 81.9 |
| Mixture ("MIX") | 120 | 104.1 | 113.5 | 12.5* | 99.1 |
| | 240 | 104.4 | 114.3 | 9.4 | 136.5 |
| Pure "DELTA-3" | 120 | 110 | 122.1 | 16.2(ns) | 54.9 |
| | 240 | 106.7 | 110 | 15.2(ns) | 66.9 |
| Pure "DELTA-2" | 120 | 98.3** | 103.2 | 8*** | 153.2 |
| | 240 | 101.6 | 116.9 | 9.7*** | 132.8 |

The superiority of compound "DELTA-2", claimed by this invention, is obvious. It is confirmed by the slightest activity of "MIX" and by the inactivity of compound "DELTA-3", at the doses administered.

IV. Therapeutic applications of the claimed compound according to this invention Compound I, as 17 beta-acetoxy (DELTA-2), is useful in therapeutics in the following cases:
(1) pituitary-gonadal dysfunction in both sexes, including some forms of infertility, at a daily dose of 25 to 100 mg;
(2) endometriosis, at a daily dose of 100 to 300 mg;
(3) certain conditions involving bone atrophy (osteoporosis), osteolysis (bone metastases of various cancers), Paget's bone disease, retardation in the bone repair process (delay in consolidation of fractures or grafts; pseudarthrosis), associated or not with hyperparathyroidism, at a daily dose of 10 to 100 mg.

Compound I (acetate) as embodied by this invention, is essentially, but not exclusively, destined for oral administration, in one of the usual pharmaceutical forms: tablets, capsules, pills or else in a liquid vehicle, as a suspension or a solution in olive oil, in gelatine capsules, or in a syrup or a linctus.

Taking the above precise dosage limits into account, according to the indications, the concentrations per unit dose should preferably be: 10 L mg, 25 mg, 100 mg.

This compound can also be administered in the form of suppositories containing 25 or 50 mg, for rectal or vaginal insertion, or in the form of a lotion or spray containing 10 mg/ml in an appropriate vehicle.

Lastly, this compound can be used in an injectable form, for intra-muscular administration, at a concentration of 25 to 50 mg per ampoule, in an acceptable lipid solvent (olive or sesame oil, benzyl alcohol etc...)

Furthermore, several clinical investigations are reported hereunder, in order to confirm the claimed compounds properties, already demonstrated in laboratory animals.

It should be taken into account the fact that the reported cases have been intentionally selected for their exemplary signification among the considerable results of extensive research in hospitals.

PART 1: Pituitary and gonadal conditions

The method of treatment of pituitary-gonadal dysfunction in both sexes has been illustrated in a first series of observations including several forms of infertility. This method consists in the administration of the 17 beta-acetate of the pure 17 alpha-ethynyl (5 alpha), 2-androsten, 17 beta-ol the preparation of which is described in the above example; for convenience this compound is abbreviated into "Compound DELTA-2" or shorter still into "DELTA-2".

This method is based on the stimulating properties of this new compound on the secretion and/or release of the FSH and LH gonadotrophins, in the absence of which neither the ovaries nor the testes can accomplish their physiological functions which are the hormonal impregnation of the target organs and reproduction.

Three exemplary observations are summarised below:

Case No. 1

Typical Klinefelter's disease with XY-XXY mosaicism

The patient was 19 years old when the following investigation was performed; the diagnosis had just been made and no treatment had been given.

This disease is a gonadal dysgenesis, irreversible by definition. The gonadotrophins, FSH mainly, are secreted and released in excessive quantities, revealing the reaction of the hypothalamo-pituitary axis to the testicular alteration.

"Compound DELTA-2" was administered orally at a dose of 10 mg/day for 15 days. The massive increase of the FSH gonadotrophin, which, already at the basal state, was sub-maximal, can have no other cause but "Compound DELTA-2".

| | CASE N°1 | |
|---|---|---|
| | Day 0 (basis) | Day + 16 (after 15 days' treatment) |
| Urinary FSH/24 hrs (mouse units*) | 80 | 260 |

*normal: <40 mouse units

N.B. This relatively ancient observation is the one which revealed to the inventor the true biological outlines of compound "DELTA-2" and instigated research in animals, as described in this specification, on hypothalamo-pituitary-gonadal interrelationships.

Case No. 2

Common Turner's disease, with a 45, XO caryotype

The diagnosis was confirmed at the age of 14 but in order not to disturb statural growth, the substitution hormone therapy was only prescribed from the age of 18 and a half.

"Compound DELTA-2" was administered orally for 30 days at a daily dose of 10 mg. The patient was then aged 18 years and 2 months.

The following table gives the biological response obtained.

| | CASE N°2 | |
|---|---|---|
| | Day 0 (basis) | Day + 16 (after 15 days' treatment) |
| Urinary FSH/24 hrs (radio-immunoassay* International units | 50.6 | 178.4 |

*normal: <30 I.U./24h

Turner's disease is also a gonadal dysgenesis, therefore irreversible by definition. As with Klinefelter's disease and for analogous reasons, the basal level of the gonado-trophins are excessive. Their important increase (here, nearly 4 times) confirm the gonadotrophin-stimulating properties of "Compound DELTA-2".

Case No. 3

Typical, common, hypogonadotrophic hypogonadism, confirmed biologically when the patient was 16 years and 3 months old, and followed for 6 years (at the time of this report). This observation is summarised in the following tables. Table IX shows (a) the hormonal variations in plasma after short treatment periods with low doses of DELTA-2, then under H.C.G.; (b) under long-term treatment at a high dose (80 mg/day) then after a short withdrawal period; (c) hormonal and sperm variations under short-time treatment periods at the high dose and variable withdrawal intervals.

Table X shows the results from three LH-RH i.v. tests, 2 of which after short "DELTA-2" treatments at a low (20 mgs/day) and middle dose (40 mg/day), prior to the H.C.G. long term treatment, the last one under "DELTA-2" at a high dose (80 mgs/day) for 6 months. Table XI gives the normal, hormonal, plasma figures for male and female adults (norms for the laboratory which performed the assays).

TABLE IX a/ Hormonal variations in plasma after short treatment periods with low doses of Delta 2, then under HCG.

Patient born in April 1957
Hypogonadotropic Hypogonadism

| | FSH (m IU/ml) | LH (m IU/ml) | Testosterone (ng/ml) | Estradiol (pg/ml) |
|---|---|---|---|---|
| Basil January 1974 | 1 | 4 | 0.6 | 17 |
| DELTA 2 10mg/d × 20 days + 12 days interval | | | | |
| 12 April 1974 | 4 | 3 | 0.6 | 25 |
| 12d. after withdrawal | | | | |
| DELTA 2 10mg/d × 10d. + 15mg/d × 7d. + 20 days interval | | | | |
| 17 June 1974 | 2 | 4 | 0.9 | 150 |
| 20d. after withdrawal | | | | |
| DELTA 2 20mg/d × 15d. from 13 to 28 July and from 13 to 28 Aug. | | | | |
| 21 Sept 1974 | 3 | 6 | 0.9 | 60 |
| 24d. after last withdrawal | | | | |
| DELTA 2 40mg/d × 15d. from 21 Dec to 4 Jan and from 21 Jan to 4 Fev. | | | | |
| 21 Feb 1975 | 3 | 2 | 0.6 | 395 |
| 17d. after last withdrawal | | | | |

Two LH-RH tests performed on 29 Apr 75 (I) and 25 July 75 (II) (table X) separated by a "Δ2" treatment: 20mg/day from 1st to 24 July
Both tests were negative.

HCG from 20 Sept 1975 to 19 Oct 1977 i.e. 25 months: 4500 IU/week; 7500 IU/week; 13000 IU/week; finally 20000 IU/week from 20 Apr 1976 to 19 Oct 1977 i.e during 18 months

| | FSH | LH | Testosterone | Estradiol |
|---|---|---|---|---|
| 6 Dec 75 | — | — | 0.86 | 20 |
| (7500 U/week during the previous 2½ months) | | | | |
| 19 March 77 | — | — | 15.4 | 77 |
| (2000 U/week for 11 months) | | | | | b/ Hormonal variations in plasma under long term DELTA 2 treatment at a high dose (11 months, 80mg/day), then after a short withdrawal period.

| | PLASMA | | | |
|---|---|---|---|---|
| | FSH (m IU/ml) | LH (m IU/ml) | Testosterone (ng/ml) | Estradiol (pg/ml) |
| HCG LAST INJECTION 19 Oct 1977 | | | | |
| DELTA 2: 80mg/d from 20 Oct 1977 | | | | |
| 19 Nov 77 | 1.9 | 4.3 | 5.2 | 29 |
| (1 month under Δ2) | | | | |

TABLE IX-continued

| | FSH | LH | Testosterone | Estradiol |
|---|---|---|---|---|
| DELTA 2 continuously 80mg/day | | | | |
| 18 Feb 1978 | 3 | 2.6 | 3.3 | 10 |
| (4 months under Δ2) | | | | |
| 22 April 1978 | 2.5 | 1.8 | 1.4 | — |
| (6 months under Δ2) | | | | |
| 7 Oct 1978 | 4.2 | 2.6 | 7.30 | 43 |
| 17 days after withdrawal of Δ2, administered for 11 months | | | | | c/ Hormonal variations and spermatogenesis under short-term treatment periods and variable withdrawal intervals.

| | PLASMA | | | |
|---|---|---|---|---|
| | F.S.H. (I.U./ml) | L.H (I.U./ml) | testosterone (ng/ml) | estradiol (pg/ml) |
| 7 October 1978 | 4.2 | 2.6 | 7.30 | 43 |
| 17 days after withdrawal of Delta 2, administered for 11 months(reminder) | | | | |
| DELTA 2: 80mg/day from 10 Oct to 13 Nov 1978 | | | | |
| 13 November 1978 | 1.8 | 2 | 0.45 | 20 |
| last day of 234 day-treatment | | | | |
| DELTA 2: Suppression on 13th Nov 1978 | | | | |
| 2 December 1978 | 3.3 | 1.8 | 3.70 | 19 |
| 20 days after withdrawal | | | | |
| 2 January 1979 | — | — | — | — |
| 50 days after withdrawal | | | | |
| DELTA 2: 80mg/day from 3rd Jan to 5th Feb 1979 | | | | |
| 5 February 1979 | 1.9 | 3.6 | 2 | 15 |
| 30 days under Delta 2 | | | | |
| DELTA 2: Suppression on 6th Feb 1979 | | | | |
| 7 April 1979 | 2.5 | 1.7 | 6 | 22 |
| 61 days after withdrawal | | | | |

| | SPERM | | | |
|---|---|---|---|---|
| | ejaculation (volume-ml) | Spermatozoa (number/mm³) | normals (%) | Living (%) |
| 7 October 1978 | 2 | 60 | 70% | 70% |
| 17 days after withdrawal of Delta 2, administered for 11 months(reminder) | | | | |
| 13 November 1978 | 1.2 | 300 | 30% | 50% |
| last day of 234 day-treatment | | | | |
| 2 December 1978 | — | — | — | — |
| 20 days after withdrawal | | | | |
| 2 January 1979 | 1.2 | 2000 | 20% | 20% |
| 50 days after withdrawal | | | | |
| 5 February 1979 | 1.5 | 1000 | 50% | 80% |
| 30 days under Delta 2 | | | | |
| 7 April 1979 | 1.5 | 5,000,000 | 75% | 75% |
| 61 days after withdrawal | | | | |

TABLE X

Results from three LH-RH i.v. in tests (100 g) performed under different situations:

| | −15 | 0 | +15 | +30 | +60 | +90mn |
|---|---|---|---|---|---|---|
| 1° 29 APRIL 1975 | | | | | | |
| 84 days after the end of a DELTA-2 treatment (40 mgs/day × 14 days) | | | | | | |
| FSH (mIU/ml) | 1.3 | 1.2 | — | 2.4 | 2.0 | 1.1 |
| LH (mIU/ml) | 0.9 | 0.6 | — | 3.2 | 1.6 | 1.4 |
| 2° 25 JULY 1975 | | | | | | |

TABLE X-continued

Results from three LH-RH i.v. in tests (100 g) performed under different situations:

| | −15 | 0 | +15 | +30 | +60 | +90mn |
|---|---|---|---|---|---|---|
| The day after the last day of a 24-day DELTA-2 treatment (20 mgs/day) | | | | | | |
| FSH (mIU/ml) | 0.2 | 0.2 | — | 1.6 | 2.1 | 1.6 |
| LH (mIU/ml) | 0.4 | 0.4 | — | 1.7 | 1 | 1 |
| 3° 22 APRIL 1978 Under DELTA-2 treatment for 6 months (80 mgs/day) | | | | | | |
| FSH (mIU/ml) | 2.1 | 2.7 | 6.2 | 15.8 | 8.8. | 10.3 |
| LH (mIU/ml) | 1.7 | 1.9 | 25 | 36 | 24 | 22 |
| Testosterone (ng/ml) | 1.4 | 2.1 | 2.1 | 2.2 | — | — |

TABLE XI

Normal, hormonal, plasma figures for male and female adults (norms for the laboratory which performed the assays)

| MALES | |
|---|---|
| FSH (m IU/ml): | 2.3 (range 0.8–4.4) |
| LH (m IU/ml): | 2.0 (range 0.5–5.0) |
| Testosterone (ng/ml): | 5.1 (range 2.8–9.9) |
| Estradiol (pg/ml): | 24.0 (range 8–45) |
| FEMALES | |
| Testosterone (mean): | 0.5 ng/ml |
| Estradiol (pg/ml) | |
| follicular phase: | mean 121 (range 54–228) |
| ovulatory peak: | mean 216 (range 140–300) |
| luteal phase: | mean 119 (range 50–210) |

We give hereunder a short discussion of Tables IX, X, XI from which it is clear that the variations of the hormone levels caused by the various therapeutic manipulations prove that compound "DELTA-2" stimulates the production of human pituitary gonadotrophins and the two testicular function. The history of this case has been the following:

(a) Between April 1974 (aged 17) and July 1975 (aged 18 3/12), compound "DELTA-2" was administered for short cures (15 to 20 days) at daily doses of 10 mg, 15 mgs, 20 mgs and 40 mgs. Plasma pituitary and gonadal hormone assays were performed each time, 10 to 20 days after withdrawal of the treatment. At each determination, an important increase of estradiol, which once reached and once exceeded the figures of the ovulatory peaks in normal women was noted.

The increase in the testosterone levels did not exceed 150% of the basal values; therefore this hormone, under this first course of treatment, scarcely exceeded the limit for the female norms and this concurs with the persistence of impuberism; the FSH and LH gonadotrophin levels were normal prior to the therapy, as is usual in this disease, and did not vary significantly (see table IX, a).

The temporary increase in estradiol and testosterone levels may be have been due
either to the direct stimulation of the endocrine testicle, by "DELTA-2" (it is well known that estradiol is of testicular origin, from either the secretion or the peripheral conversion of testosterone),
or to a rebound phenomenon after withdrawal of the treatment, further to testicular inhibition which "DELTA-2" may have caused.

The ulterior evolution of this case made this second hypothesis the more likely one: after withdrawal of an intensive, prolonged (11 months) DELTA-2 treatment, at a high dose (80 mg/day), progressive improvement led to hormonal normalisation and increasing spermatogenesis (which went together with the final clinical normalisation) (see Table IX, b and c).

(b) The first two stimulation tests with 100 μg LH-RH performed in April and July 1975, L remained negative (see Table X and the origin of this could be:
either a lesional pituitary insufficiency,
or the incapacity of a pituitary that was inert since never stimulated or could not react to the first sollicitations of the hypothalamic hormone from which it depends (and this was to be confirmed three years later).

(c) Because of the physchological repercussions of the state of impuberism (the patient was then 18 years and 5 months old), a stimulatory treatment was applied between September 1975 and October 1977 with exogenous human chorionic ganodatrophin (H.C.G.) (see Table IX,a).

After two and a half months of H.C.G., at the weekly dose of 7,500 International Units (I.U.) in 3 injections, the plasma testosterone was not above the levels reached after the short cures of "DELTA-2"; 20,000 I.U. per week were needed to attain important figures (triple the normal masculin mean). As for estradiol, though responding to the ganodotrophin, under H.C.G., even at strong doses, it never exceeded the highest levels recorded after administration of compound "DELTA-2". To conclude, it can therefore be considered that this compound at the doses administered and for the indicated periods, produced stimulating effects that were at least equivalent to those of 7,500 I.U. of H.C.G. per week with regard testosterone, and at least equivalent to 20,000 I.U. of H.C.G. per week with regard estradiol.

(d) H.C.G. was withdrawn after 25 month's continuous treatment. On the day following the last injection, it was replaced by steroid "DELTA-2" which was administered for 11 months at a daily dose of 80 mg.

Plasma determinations were performed: 1 month, 4 months and 6 months after the beginning of this treatment but without it being interrupted:
both gonadotrophins were found in the blood at normal levels;
testosterone, which under 20,000 I.U. week H.C.G. reached 15.4 ng/ml, remained remarkably within normal limits under "DELTA-2" at least 4 months after withdrawal of the gonadotrophins; later it decreased, but at the sixth month, its level had still remained within the zones of normal male puberty (see table IX, b).

Because of the very brief biological half-life of pituitary gonadotrophins on the one hand and on the other, by definition, the irreversible nature of hypogonadotropic hypogonadisms, the maintenance of testosterone at male levels six months after the last gonadotrophin injection, can only be explained by the pituitary and/or (direct) testicular stimulation caused by the "DELTA-2" steroid.

This supposition is, on the other hand, supported by:
the increase in volume of the testes (approx. 3.5×2.5 cm - i.e. more than 1 cm in both axes than under H.C.G.), and
the progression of clinical virilisation under "DELTA-2".

(e) A third LH-RH test (see table X), performed under 80 mg/day of steroid "DELTA-2", at the end of the sixth month of treatment, on Apr. 22, 1978, caused massive, prolonged release of both gonadotrophins:

the FSH basal level was multiplied by 7 at the 30th minute of the test and by 5 at the 90th minute;

the LH basal level was multiplied by 14 as of the 15th minute, then by 20 at the 30th minute; at the 90th minute, it was still 13 times the basal figures.

Such a response reveals the existence of a production of these hormones which is much higher than normal. The excess of these which cannot be entirely released into the organism, is stored in the pituitary.

After LH-RH stimulation, analogous results are obtained in all conditions of agonadism: either anatomic (castration, agenesis), or functional (menopause), but the response obtained from our patient is different from those from agonadism conditions. In these last cases:

it is always FSH that reacts more violently, and particularly, the increase of the gonadotrophins scarcely exceeds 3 or 4 times the basal figures.

(f) After 11 months continuous administration at the daily dose of 80 mgs, treatment with "DELTA-2" was withdrawn, on Sept. 20, 1978.

Seventeen days later (see Table IX, c), the analysis showed an important increase in the plasma levels of testosterone and estradiol and revealed the presence of a few, though, normal, mobile, spermatoza.

The treatment was started again twice at the same dose for about one month: each time under treatment the hormone levels were reduced and then increased from the third or fourth week after withdrawal; spermatogenesis followed the same general evolution, but with some delay, linked with the physiologic duration of the spermatogenic cycle (approximately 6 weeks).

These results suggest that one of the mode of action of compound DELTA-2 lies in direct inhibition of the testis on both the hormonal and spermatogenic levels. The rapid increase of all the parameters observed after withdrawal of the treatment corresponds in this case to a rebound phenomenon.

Further results showed that the rebound phenomenon after DELTA-2 withdrawal can be both prolonged and progressive.

Sixty days after the end of the treatment, in fact, the plasma testosterone of the patient again exceeded the mean levels of healthy, male, adults (6 ng vs. 5.1 ng/ml) and the sperm count went from 1000 to 5,000,000/mm$^3$, three quarters of which were normal and mobile.

Clinically, the patient has now become morphologically and fonctionally normal.

Hypogonadotrophic hypogonadism is a congenital disease, irreversible by definition; it is characterised by an impuberism condition of a central origin: either hypothalamic, as in this case, or pituitary, which can only be corrected by a hormonal substitution treatment with exogenous pituitary gonadotrophins.

Amongst these, human chorionic gonadotrophin (H.C.G.), which possesses a practically exclusive LH activity, causes secretion of testicular hormones and clinical virilisation of the patient, but only FSH, which is dominant in preparations derived from urine of postmenopausal women (HMG) can stimulate the spermatogenetic function, hence the volume of the testis.

Consequently, hypogonadotrophic hypogonadism is an ideal situation for the study of substances likely to stimulate the gonadotropic functions of the pituitary, and the gonad hormone secretion as well as reproduction.

The data accumulated in the case above prove that steroid "DELTA-2" stimulates the secretion of the two pituitary gonadostimulins:

LH, hence normalisation of the plasma levels of testicular hormones and virilisation of the patient, FSH, hence increase of testicular volume and the appearance of spermatozoa in the sperm.

Similar results can be obtained with HMG and HCG gonadotrophins only after long-lasting uninterrupted stimulation (2 to 3 years).

The fact that these results were noted after treatment with "DELTA-2" is the demonstration that this compound induces secretion and/or release of endogenous FSH and LH gonadotrophins.

If the two LH-RH tests, performed before treatment with the HCG gonadotrophin, remained negative, it was because the pituitary of the patient had never been solicited before by the positive feed-back action of the gonadal steroids and also because the stimulation periods with steroid "DELTA-2" had been too short and/or too spaced out to trigger off the gonadal-pituitary mechanism.

This is a very likely interpretation if one refers to the completely analogous case of hypothalamic hypogonadism of the Kallman-De Morsier syndrome (olfactory-genital dysplasia), in which it is now known that before obtaining hormonal response, it is necessary to stimulate the pituitary with repeated administrations of LH-RH at high doses.

Once the pituitary of our patient was sensitised by the testicular hormones secreted under the effect of the prolonged treatment with HCG, it became capable of producing gonadotrophins under the stimulating effect of "DELTA-2".

The massive, prolonged response at the third LH-RH test corresponds to the excessive FSH and LH production caused by the pituitary stimulation with "DELTA-2", which had led to the formation of considerable stocks as revealed by their release after the LH-RH injection.

To conclude, this outstanding case proves that pure steroid "DELTA-2" stimulates the production of both pituitary gonadotrophins in man, either by direct action on the pituitary, or further to a rebound phenomenon, following direct testicular suppression, or else by both of these.

Whatever the explanation of the mechanism implied, this activity is different and even opposed to that attributed by Huffman (U.S. Pat. No. 2,996,524) to his (then unknown) mixture of isomers and the therapeutic usefulness of this discovery is considerable.

Part 2. Endometriosis

Another particularly useful and unexpected field of therapeutic application revealed by the present invention is that of endometriosis.

This widespread disease is manifested, amongst others, by intense pain towards the end of the menstrual cycle, due to proliferation under the effect of physiologic estrogens, of fragments of endometrial tissue disseminated outside the uterine cavity.

Treatment of this condition not infrequently requires surgical removal or drug suppression of the ovarian function.

The clinical results obtained by "DELTA-2" in a group of ten patients in a Gynaecology Ward of a University Teaching Hospital are summarised hereafter.

Ten patients, from 18 to 41 years of age, suffering from evolutive ovarian, peritoneal and/or uterine endometriosis, were treated from 2 to 4 months with compound "DELTA-2" at a daily dose of 100 mgs.

Before treatment, coelioscopy enabled, in all cases:
1. confirmation of the diagnosis,
2. the initial topography of the lesions to be drawn up
3. sampling of the peritoneal liquid and biopsies for cytological and histological examination, respectively.

The following results were noted:

A—Menses (a) five patients became amenorrhoeic at the end of the first month,
(b) three others, at the end of two months,
(c) the last two one presented very scanty menstruations.

B—Pain

Spontaneous pain improved considerably from the first month of treatment, the best results being obtained in the diffuse forms.

Pain provoked by vaginal examination no longer existed.

C—Control coelioscopy

It has been performed until now in three cases, where the following was noted:
a quiescent aspect of the ovaries, devoid of follicles,
disappearance of ovarian endometriosis clusters,
replacement of peritoneal endometriosis with cicatricial fibrosis tissue.

Part 3. Bone pathology

In a third series of observations, there have been illustrated the method of treatment of certain conditions involving bone atrophy (osteoporosis), osteolysis (bone metastases of various cancers), Paget's disease, retardation in the bone repair process (delay in the consolidation of fractures or grafts; pseudarthrosis) associated or not with hyperparathyroidism, consisting in the administration of the same compound "DELTA-2", at a daily dose of 10 to 100 mg.

It is well known that the bone is formed of an organic matrix and mineral salts (essentially calcium phosphate), the former used as a support for the latter. It is also known that bone is constantly remade by a double, parallel and concomitant process of destruction (osteolysis) and repair (osteogenesis).

Until the end of the growth period, osteogenesis exceeds osteolysis; in normal adults the two processes are balanced but in certain pathologic conditions, osteolysis exceeds osteogenesis and the result is bone atrophy, which can be either diffuse or localized.

The osteolytic process provokes the increased elimination of the two main components of bone: calcium and hydroxyproline. The latter is a specific amino-acid of the protein of bone collagen. Bone turnover needs the participation of certain enzymes, i.e. phosphatases. Alkaline phosphatase participates in the formation of bone: its low or excessive levels in plasma reveal respectively slowed or accelerated bone formation. The highest levels are characteristic of Paget's bone disease, which is an outstanding model of very accelerated turn-over.

The result is that the activity of bone tissue can be determined very reliably by a few simple assays:
serum alkaline phosphatase,
urinary hydroxyproline,
the ratio between calcium and creatinin in urine collected during 2 hours after 12 hours of fasting ("Nordin ratio").

Seven outstanding cases of three different types of osteolytic process are summarised below. The effect of compound "DELTA-2" will be appreciated in each one by the modification of the biologic parameters and/or by radiographs.

These observations can be therefore classified into three groups:
group A, comprising observations identified by "Case A/1" and "Case A/2";
group B comprising observations identified by "Case B/1" and "Case B/2"
group C, comprising observations identified by "Case C/1" "Case C/2" and "Case C/3".

GROUP A: The two cases of this group concern a congenital disease: osteogenesis, imperfecta, characterized by genetic brittleness of the long bones which causes numerous spontaneous fractures, the repair of which causes deformity.

Case No. A/1

The patient, 11 years of age at the beginning of the observation, was followed to the age of 17.

He presented in several respects an atypical form of the disease, amongst others, characterized by:
severe bone atrophy, the cortical bone being reduced by 4/5ths,
a constant hypercalcaemia, suggesting the existence of a parathyroid, osteolytic reaction per se.

During the three years wich compound "DELTA-2" was administered, and with no other simultaneous therapy, and despite the very low daily dose (5 mg),
the 24 hours calciuria level was maintained within the physiological limits, and
the Nordin ratio always remained quite normal (N:<0.15), with one exception, in September 1974, at the time of the last fracture;
the calcaemia levels, with one exception, were always lower under "DELTA-2" than those of the calcitonin therapy period.

Radiologically, in this case, bone repair was revealed by a definite thickening of the control bone of the femurs and tibias.

Case. No. A/2

This is a case of a common osteogenesis imperfecta of the "tarda" type, the first spontaneous fracture occuring at the age of 3 and the 46th (and last) at the age of 17.

However, three years later, further to trauma, the femur broke at the end of a intramedullary pin inserted four years previously.

Treatment with Compound "DELTA-2" was started after this traumatic fracture, at a daily dose of 10 mg.

Its effect was manifest with the ending of the osteolytic process from the end of the first month and confirmed by the decrease in the figures of the three tests (viz. Table below): up to normal for the plasma and urinary calcium; up to the limits of the normal for Nordin's ratio, which is remarkable in so short a time and taking the basal figure into account.

| CASE N°A/2 | | |
|---|---|---|
| | Before "DELTA-2" 7th November 1977 | After 29 days of "DELTA-2" 6th January 1978 |
| Plasma calcium (mg/1) | 104 | 100 |
| Urinary calcium (mg/24 hrs) | 264 | 195 |
| $\frac{Ca}{Cr}$ ratio* in urine after fasting | 0.47 | 0.199 |

*(N:<0,15)

The fracture was consolidated after two and a half months despite the constitutional bone fragility.

GROUP B: The two observations of this group concern metabolic anomalies of the skeleton, of an indetermined origin, in two young and apparently healthy subjects.

Case No. B/1

This 35 year old woman sustained a serious, multiple fracture of the right tibia after minimal trauma.

Osteosynthesis was performed under good conditions; however, consolidation was still not obtained one year later, despite the anabolic steroid treatment, but only in February 1977, twenty months after the operation.

Because of the undefined conditions of this practically spontaneous fracture, the patient is being followed biologically after healing.

As seen on the following table, one month after the radiologic confirmation of the consolidation (March 1977), the biologic signs of an osteolytic surge (though clinically nil) appear: hypercalciuria at 450 mg/24 h (normal<250 mg) and Nordin's ratio at 0.22.

After 30 days' treatment with "DELTA-2", at a low daily dose (5 mg), the two parameters returned to normal 131 mg and 0.073 respectively); they remained unchanged 53 days after the withdrawal of the treatment (130 mg and 0.08 respectively) but they become pathological again in October 1977, i.e. 144 days after the end of the "DELTA-2" treatment: calciuria at 550 mg/24 hrs and a Nordin ratio of 0.21.

A second course with steroid "DELTA-2" (20 mg/day at first, then 5 mg/day) causes normalisation again of both parameters, though less rapidly than the first time, which is why the low dose treatment was continued for several months longer.

with osteomyelitis of the foot at the age of 7, which caused complications and numerous, continuous consequences, and which ended, amongst others, with complete prostheses of both hips, the last one in November, 1977.

A first analysis, on 2nd December, revealed the biologic signs of an osteolytic process. Treatment with "DELTA-2" was immediately started at a dose of 10 mg/day and on 50th day of this treatment (see below) the urinary hydroxyproline was normalised and Nordin's ratio, which was not initially pathologic, was reduced by nearly a third.

| CASE N°B/2 | | |
|---|---|---|
| | Base | After 50 days' treatment with "DELTA-2" 10 mg/day |
| Urinary hydroxyproline (mg/24h)* | 45 | 30 |
| Nordin's ratio (Ca/Cr) | 0.132 | 0.095 |

*Urinary hydroxyproline N:<35 mg/24hrs.

GROUP C: The three observations of this group are patients suffering from Paget's evolutive bone disease who were previously treated with calcitonin at various doses and periods of time.

Compound "DELTA-2" was started a long time after withdrawal of the previous treatment in the three cases. The results were evaluated according to the only two biological parameters unanimously considered characteristic of the evolution of this disease, namely, alkaline phosphatase and hydroxyproline in 24-hours urine.

There was a decrease in the three cases under the influence of the treatment, thereby showing that there is a reduction in the high turnover characteristic of the disease.

Case No. C/1

Man, aged 54. Evolutive Paget's bone disease, diagnosed in 1975, treated with calcitonin for a long time (50 U every two days to 160 U every 2–3 days) and analgesics.

| CASE N°C/1 | | | |
|---|---|---|---|
| | Before "DELTA-2" | After 60 days of | After 94 days of "DELTA-2" 20 mg/day |

| CASE N°B/1 | | | | | | | |
|---|---|---|---|---|---|---|---|
| | Before "DELTA-2" 17 March 77 | After 29 days of "DELTA-2" 5 mg/day 12 May 77 | 53 days after withdrawal of "DELTA-2" 12 July 77 | 144 days after withdrawal of "DELTA-2" 11 Oct. 77 | After 30 days of "DELTA-2" 20 mg/day 22 Nov. 77 | After 53 days of "DELTA-2" 20 mg/day 15 Dec. 77 | After 40 days of "DELTA-2" 5 mg/day 24 Jan. 78 |
| Urinary calcium (mg/24h) | 450 | 131 | 130 | 550 | 193 | 290 | 289 |
| Nordin's ratio Ca/Creatinine | 0.22 | 0.073 | 0.08 | 0.21 | 0.24 | 0.09 | 0.09 |

Case No. B/2

The pathologic history of the skeleton of this woman, aged 34 (and otherwise in excellent condition) started

| | 14 April 1978 | "DELTA-2" (10 mg/day) 14 June 1978 | for 20d. 18 July 1978 |
|---|---|---|---|
| Alkaline | 128 | 106 | 86 |

-continued

CASE N°C/1

| | Before "DELTA-2" 14 April 1978 | After 60 days of "DELTA-2" (10 mg/day) 14 June 1978 | After 94 days of "DELTA-2" 20 mg/day for 20d. 18 July 1978 |
|---|---|---|---|
| phosphatase (international units/1)* | | | |
| Urinary hydroxyproline (mg/24hrs)** | 33 | 28 | 20 |

*normal: 9-35 I.U.
**normal: 15-35 mgs/24hrs

Case No. C/2

Female, aged 65. Diffuse, evolutive Paget's bone disease, diagnosed in 1973 and periodically treated with calcitonin (50 U/day) and analgesics.

CASE N°C/2

| | Before "DELTA-2" 3 April 1978 | Under treatment with "DELTA-2" 20 mg/d × 40 days + 7.5 mg/d × 10 days 11 July 1978 | Under treatment with "DELTA-2" 20 mg/d × 40 days 11 September 78 |
|---|---|---|---|
| Alkaline phosphatase (I.U./1) | 76 | 80 | 70 |
| Urinary hydroxyproline (mg/24hrs) | 13 | — | 11 |

CASE N°C/3

Female, aged 56. Widespread, evolutive Paget's disease, diagnosed in 1970, treated for six years with calcitonin (from 25 to 160 v/day) with few results.

| | Before "DELTA-2" 2 months after Calcitonine June 1978 July 1978 | After 30-32 days of "DELTA-2" 20 mg/day 23 Aug. 1978 31 Aug. 1978 | After 45 days of "DELTA-2" 20 mg/day 5 Sept. 1978 |
|---|---|---|---|
| Alkaline phosphatase (units/1) | 92* 112* | 2129** | 886* |
| Urinary hydroxyproline (mg/24hrs) | 300 194 | 100 | 92 |

*Kind & King units (normal: <13)
**International units (Laboratory norms: normal between 60 and 200)

What I claim is:

1. Process for obtaining pure 17 alpha-ethynyl (5 alpha), 2-androsten, 17 beta-ol, i.e. without the delta-3 isomer, comprising the steps of: in a first stage, a mixture of 17-keto (5 alpha), 2-androsten and 17-keto (5 alpha), 3-androsten is oxidised by Jones reagent; in a second stage, the oxidised reagent mixture is purified by silica gel column chromatography and the benzene eluate collected, in a third stage, this eluate is reacted with acetylene in a solution of potassium in t-amylalcohol and the reaction product is collected by extraction and recrystallisation.

2. Method of treatment of endometriosis, comprising the administration of the 17 beta-acetate of pure 17 alpha-ethynyl (5 alpha), 2-androsten, 17 beta-ol at a daily dose of 100 to 300 mg.

3. A process for preparing the delta-2 isomer 17 alpha-ethynyl (5 alpha) 2 androsten, 17 beta-ol unmixed with its delta-3 isomer, comprising the steps of:
   (a) treating a mixture of the isomers 17-keto (5 alpha), 2-androsten and 17-keto (5 alpha), 3-androsten with Jones Reagent to oxidize the 17-keto (5 alpha), 3-androsten;
   (b) collecting the unoxidized 17-keto (5 alpha), 2-androsten; and
   (c) forming the pure delta-2 isomer 17-alpha-ethynyl (5 alpha), 2-androsten, 17 beta-ol from the unoxidized 17-keto (5 alpha), 2-androsten.

4. The process of claim 3 wherein said treating step further comprises
   (i) adding Jones Reagent to a solution of said mixture of step (a);
   (ii) adding methanol;
   (iii) distilling the solvent of the solution in step (i);
   (iv) taking up the residue from the previous step in water;
   (v) filtering and washing the precipitate from the previous stop;
   (vi) dissolving said precipitate in methylene chloride;
   (vii) drying the organic solution from the previous step with sodium sulphate; and
   (viii) distilling the resultant of the previous step; wherein said collecting step further comprises purifying the residue from the previous step by silica column chromatography and recovering pure 17-keto (5 alpha), 2-androsten by elution with benzene.

5. A process for obtaining the pure delta-2 isomer from a mixture of 17-keto (5 alpha), 2-androsten and 17-keto (5 alpha), 3-androsten comprising the steps of:
   (a) treating said mixture with Jones Reagent to oxidize the 17-keto (5 alpha), 3-androsten; and
   (b) collecting the unoxidized 17-keto (5 alpha), 2-androsten.

6. The process of claim 5 wherein said treating step further comprises:
   (i) adding Jones Reagent to a solution of said mixture of step (a);
   (ii) adding methanol;
   (iii) distilling the solvent of the solution in step (i);
   (iv) taking up the residue from the previous step in water;
   (v) filtering and washing the precipitate from the previous step;
   (vi) dissolving said precipitate in methylene chloride;
   (vii) drying the organic solution from the previous step with sodium sulphate;

(viii) distilling the resultant of the previous step;
wherein said collecting step further comprises purifying the residue from the previous step by silica column chromatography and recovering pure 17-keto (5 alpha), 2-androsten by elution with benzene.

7. The process of claim 3 and further comprising the step of forming the 17 beta-acetate from the pure 17 alpha-ethynyl (5 alpha), 2-androsten, 17 beta-ol.

* * * * *

UNITED STATES PATENT AND TRADEMARK OFFICE
CERTIFICATE OF CORRECTION

PATENT NO. : 4,278,668
DATED : July 14, 1981
INVENTOR(S) : Nicolas Gueritee

It is certified that error appears in the above—identified patent and that said Letters Patent is hereby corrected as shown below:

Column 8, line 38, delete "gonadontrophins" and insert --gonadotrophins--.
Column 9, line 31, delete "+260.3" and insert --$\pm$260.3--.
Column 11, line 43, delete "10 L mg" and insert --10 mg--.
Column 13, line 58, delete "months" and insert --months)--.
Column 16, line 4, delete "L".

Signed and Sealed this

Ninth Day of February 1982

[SEAL]

Attest:

Attesting Officer

GERALD J. MOSSINGHOFF

Commissioner of Patents and Trademarks